United States Patent [19]
Hochstrasser

[11] Patent Number: 5,773,645
[45] Date of Patent: Jun. 30, 1998

[54] TWO-DIMENSIONAL ELECTROPHORESIS DEVICE

[75] Inventor: Denis François Hochstrasser, Geneva, Switzerland

[73] Assignee: Bio-Rad Laboratories, Inc., Hercules, Calif.

[21] Appl. No.: 851,829

[22] Filed: May 5, 1997

[51] Int. Cl.$^6$ .......................... G01N 27/26; G01N 27/447
[52] U.S. Cl. .......................... 204/456; 204/466; 204/606; 204/616
[58] Field of Search .................................. 204/456, 466, 204/467, 606, 616, 617, 618

[56] References Cited

U.S. PATENT DOCUMENTS

| 4,130,470 | 12/1978 | Rosengren et al. | 204/451 |
| 4,874,490 | 10/1989 | Hochstrasser | 204/451 |

Primary Examiner—Kathryn L. Gorgos
Assistant Examiner—John S. Starsiak, Jr.
Attorney, Agent, or Firm—Townsend and Townsend and Crew LLP

[57] ABSTRACT

A strip gel that may be water-swellable and a slab gel are combined on a common support for two-dimensional electrophoresis, with the strip gel isolated from the slab gel by a fluid-impermeable and electrically insulating barrier, which is preferably one wall of an enclosure that forms a reservoir for containing the strip gel. The first dimension separation is performed by placing the liquid sample and buffer in the reservoir to cause the gel to swell and to load it with sample, then passing an electric current through the reservoir. The barrier, which is joined to the support in an easily breakable manner, is then removed, and the strip gel is placed in contact with the slab gel for the second dimension separation.

10 Claims, 5 Drawing Sheets

TWO-DIMENSIONAL ELECTROPHORESIS DEVICE

This invention resides in the field of two-dimensional electrophoretic separations.

BACKGROUND OF THE INVENTION

Two-dimensional electrophoresis is a useful technique for separating complex protein mixtures, often providing a much higher resolving power than that obtainable in one-dimension separations.

The technique permits component mixtures to be separated according to two different sets of properties in succession, and lends itself to a variety of different combinations of separation parameters. One combination is separation based on charge followed by separation based on molecular weight. Another is separation in a gel of one concentration followed by separation in a gel of the same material but of another concentration. Two-dimensional separations have also been used to create a stepwise change in pH, to separate first in a homogeneous gel and then in a pore gradient gel, to separate in media containing first one protein solubilizer and then another, or in media containing a protein solubilizer first at one concentration and then at another concentration, to separate first in a discontinuous buffer system and then in a continuous buffer system, and to separate first by isoelectric focusing and then by homogeneous or pore gradient electrophoresis. Combinations such as these can be used to separate many kinds of components, including serum or cell proteins, bacterial proteins, non-histone chromatin proteins, ribosomal proteins, mixtures of ribonucleoproteins and ribosomal proteins, and nucleic acids.

The first dimension of a two-dimensional electrophoresis system is typically performed in an elongate rod-shaped gel having a diameter in the vicinity of 1.0 mm, with migration and separation occurring along the length of the rod. Once the solutes have been grouped into individual zones along the rod, the rod is placed along one edge of a slab gel and the electric current is imposed across the rod and slab in a direction perpendicular or otherwise transverse to the axis of the rod. This causes the migration of solutes from each zone of the rod into the slab gel, and the separation of solutes within each zone.

Difficulties in two-dimensional electrophoresis arise in the handling of the rod-shaped gel after the first dimension separation has occurred and in placing the gel in contact with the slab gel to prepare for the second dimension separation. The first dimension separation is generally performed while the rod gel is still in the tube in which it was cast. Once the separation in the tube has been performed, the rod is physically removed from the tube, then placed along the exposed edge of the slab gel. The extraction of the rod from the tube and the act of placing it along the slab gel edge require delicate handling, and even with the exercise of great care, the gel is often damaged and the solute zones are distorted or disturbed. Alignment and full contact of the rod with the slab gel are important for achieving both electrical continuity and unobstructed solute migration between the gels. Furthermore, considerable time is involved in the handling and placement of the rod, and errors can result in loss of data. Gel strips can be used as alternatives to the rod, but are susceptible to similar difficulties, opportunities for error, and a lack of reproducibility.

Many of these problems are eliminated by the gel packages that contain both the elongated first dimension gel and the slab-shaped second dimension gel in a common planar arrangement that permits the two separations to be done in succession without any intervening insertion or removal of either gel. One such arrangement and method of use are disclosed in U.S. Pat. No. 4,874,490, issued Oct. 17, 1989, entitled "Pre-Cast Gel Systems for Two-Dimensional Electrophoresis," Denis F. Hochstrasser, inventor, with corresponding European Patent No. 0 366 897 B1, of Bio-Rad Laboratories, Inc., specification published Sep. 28, 1994. The present invention provides a new gel pre-cast gel structure and method.

SUMMARY OF THE INVENTION

This invention resides in a pre-cast two-dimensional gel system, with the gels for each of the two dimensions of the separation retained and used on a common support. The first dimension gel is an elongate strip arranged to receive an electric current in the longitudinal direction of the strip, while the second is a slab with an edge facing the strip, and preferably parallel to it. The strip and slab are isolated from each other by a barrier that is fluid-impermeable (or fluid-retaining) and electrically insulating, yet removable. In preferred embodiments, the barrier is one wall of a receptacle surrounding the strip, the receptacle capable of retaining a liquid, notably the sample itself diluted in a buffer solution. In certain embodiments of this invention, the strip is a dry gel that swells upon imbibition of water or an aqueous solution, such that the sample diluted in aqueous buffer will fully wet and swell the strip. For strips that require being kept dry prior to use, the receptacle can further contain a removable moisture-impermeable seal that seals the strip against exposure to environmental moisture. A convenient construction for the support is a pair of flat parallel plates, one plate being greater in length than the other along one dimension to leave part of the inner surface of the longer plate exposed. The slab gel is then retained in the space between the plates while the strip gel is adhered to the longer plate on the exposed region, preferably with a gap between the strip gel and the closest edge of the shorter plate.

In use, the first dimension separation is performed with the strip isolated from the slab by the fluid-retaining and electrically insulating barrier. The barrier can be a solid retaining wall with an air gap on the slab side of the wall, in which case electrical insulation can be achieved by the air gap or by both the air gap and the retaining wall. In certain configurations of the invention, the air gap is a preferred feature since it permits the barrier to be located on the exposed portion of the longer plate and promotes easy removal of the barrier. Once the first dimension separation is performed, the barrier is removed and the two gels are placed in contact for the second dimension separation.

Details of these and other features of the invention will be apparent from the description that follows.

DETAILED DESCRIPTION OF THE INVENTION AND PREFERRED EMBODIMENTS

Figure 1:
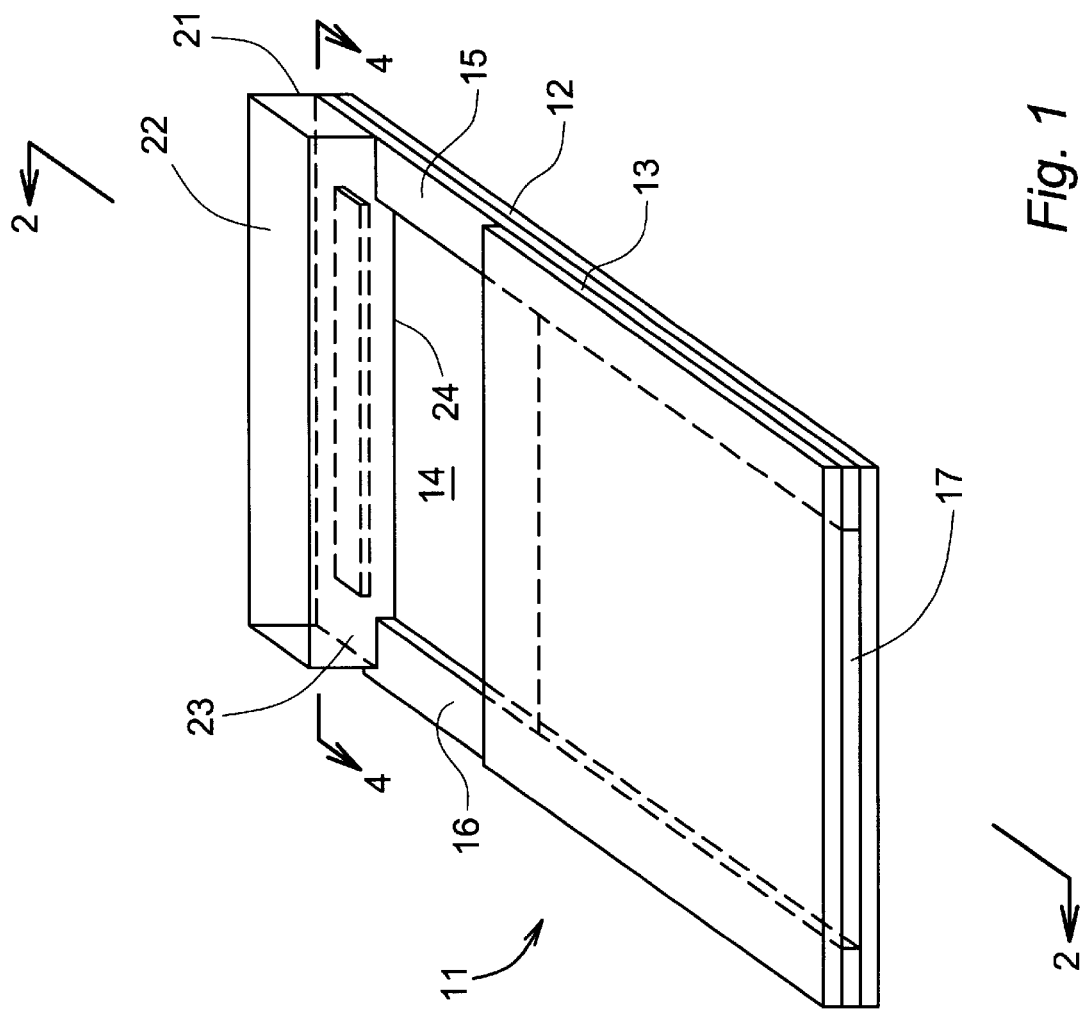
FIG. 1 is a perspective view of a pre-cast two-dimensional gel cassette in accordance with the present invention.

This invention is generally applicable to any two-dimensional separation, and finds its greatest utility in procedures in which one type of separation is performed in the first dimension (the elongate strip) and another in the second dimension (the slab). The first dimension, for example, can be a native gel, dry or swollen, or a gel containing a carrier ampholyte or a detergent. As other examples, the gels can be those specifically formulated for the separation of DNA—for example, one restriction enzyme can be used in the first dimension and another in the second dimension, or a restriction enzyme can be used in the first dimension and a denaturing agent in the second dimension. Other examples will be readily apparent to those knowledgeable in electrophoresis.

In further examples, the first dimension can contain a pH gradient in the direction of the longitudinal axis of the strip, and the second dimension either a pH gradient in the direction perpendicular to the strip or no gradient at all. The pH gradient in the strip can be formed in a variety of different ways. It may for example be a matrix with immobilized groups that are either charged to form a pH gradient or chargeable to form such a gradient. Alternatively, the pH gradient can be formed by carrier ampholytes that are not immobilized in the strip matrix.

Strips containing immobilized groups are known in the art and commercially available. Examples are disclosed in U.S. Pat. No. 4,130,470 (Rosengren et al., issued Dec. 19, 1978), the contents of which are incorporated herein by reference. The matrix may be a solid support material such as a granular, fibrous, or membrane material, or it may be a gel. Examples of matrix materials are polyacrylamide, cellulose, agarose, dextran, polyvinylalcohol, starch, silicon gel, and polymers of styrene divinyl benzene, as well as combinations of these materials. Examples of positively charged or chargeable groups are amino groups and other nitrogen-containing groups. Examples of negatively charged or chargeable groups are carboxylic acid groups, sulfonic acid groups, boronic acid groups, and phosphonic or phosphoric acid groups, as well as esters of these acids. Other examples will be readily apparent to those skilled in the art. Immobilization of the groups on the matrix can be achieved by covalent bonding or any other means that will secure the positions of the groups and prevent their migration under the influence of an electric field or due to the movement of fluids or solutes through the matrix. A preferred means of incorporating charged groups into a polymeric gel matrix is by copolymerizing charged monomers or charged crosslinking agents with the gel monomers.

The concentration of the groups will preferably vary in a monotonically increasing or decreasing manner to form an immobilized pH gradient suitable for isoelectric focusing. The specific concentrations are not critical to the invention and will vary according to the needs of the separation. Typically, the concentration of the charged groups will range from about $10^{-2}$M to about $10^{-4}$M in the gel. The elongate strip is also preferably one that is dry prior to use, but swellable upon imbibition of water. Dry strips that contain immobilized pH gradients are available from Pharmacia Biotech AB, Uppsala, Sweden.

The slab gel will generally be an aqueous gel, examples of which are polyacrylamide gels, starch gels, and agar gel, with a range of gel concentrations and porosities. The gel can be of uniform concentration or contain a concentration gradient, with or without solubilizers or with solubilizers of varying types and concentrations, and with continuous or discontinuous buffer systems. The various types of gels will be readily apparent to those skilled in the art.

The drawings provide a detailed view of one illustrative embodiment of this invention.

Figure 2:
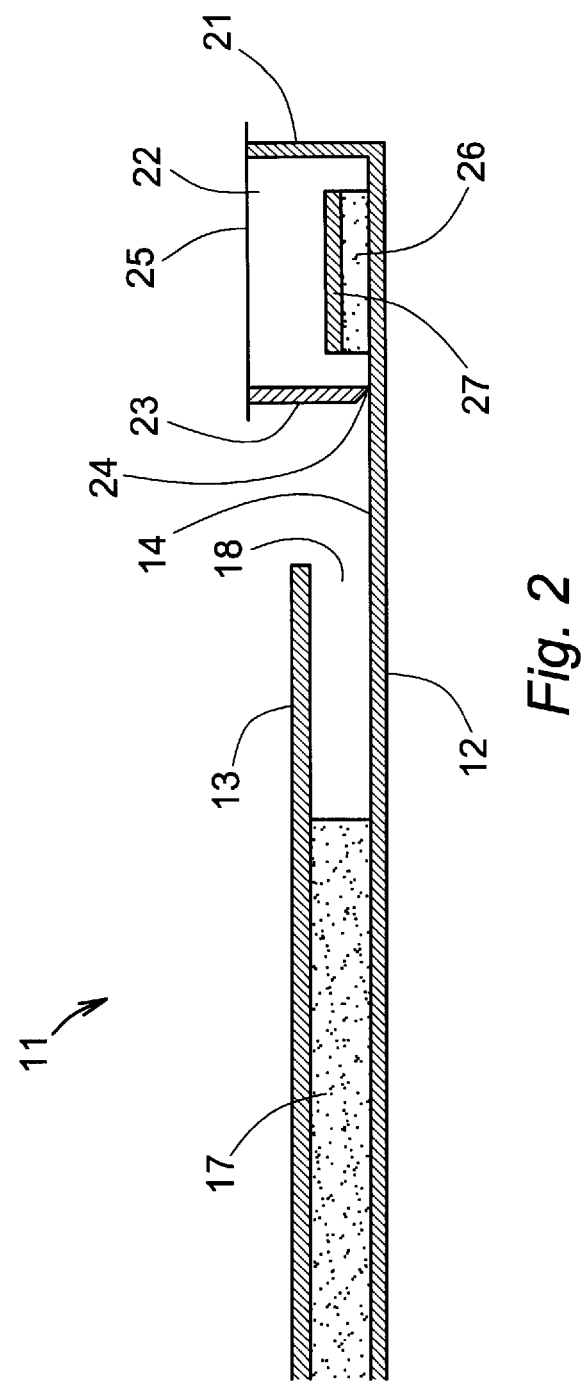
FIG. 2 is a longitudinal cross section of the gel cassette of FIG. 1, taken along the line 2—2 of FIG. 1.

The perspective view of FIG. 1 and the longitudinal cross section of FIG. 2 depict a pre-cast gel cassette 11 in accordance with this invention, the structural members of the cassette consisting of two flat plates of unequal length 12, 13, the shorter plate 13 having three edges aligned with three edges of the longer plate 12 and leaving a portion 14 of the inner surface of the longer plate exposed. In alternative constructions, still within the scope of this invention, the cassette is constructed without exposing a portion of the longer plate. The gap between the two plates is set by a pair of spacers 15, 16 positioned along the lateral edges of the plates, and the slab gel 17 occupies a portion of the gap. The plates 12, 13 and spacers 15, 16 will either be of unitary construction formed by molding or welding, or held together by clamps (not shown) of conventional construction well known to those skilled in the manufacture or use of slab gel sandwiches and cassettes. A strip 18 of the gap adjacent to the exposed portion of the longer plate is left empty, for reasons that will be apparent from the description below pertaining to the method of use.

Along the exposed portion 14 of the longer plate is an enclosure 21 forming a reservoir 22 for the retention of liquids in a manner keeping them out of contact with the slab gel 17. One wall 23 of the enclosure (the wall facing the slab gel 17) is constructed so that its joint line 24 is easily breakable by manual pressure. As a result, this wall 23 can be quickly and cleanly removed after the first dimension separation is completed. The joint line 24 can for example be scored or made of a weaker material than the remainder of the enclosure 21, or any other means of forming a connection that is easily broken yet capable of retaining liquid before being broken. The remaining walls of the enclosure 21 are preferably of a hydrophobic material. The top of the enclosure 21 can be sealed by a removable strip of moisture-impermeable material 25, both to protect the contents of the reservoir 22 from damage during storage and transportation and to keep the contents dry prior to use. The seal 25 is preferably one that can be removed by peeling away with finger pressure.

A strip of dry immobilized pH gradient gel 26 with a plastic backing strip 27 is placed inside the reservoir 22. As explained elsewhere in this specification, possibilities for the strip in general include a pre-cast gel, a dry native gel, or a dry immobilized pH gradient gel. In the arrangement shown in FIG. 2, the plastic-backed gel is placed with the gel side 26 contacting the support plate 12. The gel can be placed in the reverse direction as well, but the arrangement shown in the drawing is preferred since the gel 26 will adhere to the plate 12. The dry gel and plastic backing do not occupy the full volume of the reservoir 22, the reservoir instead leaving clearance both above the gel and along its sides for liquid access.

Figure 3:
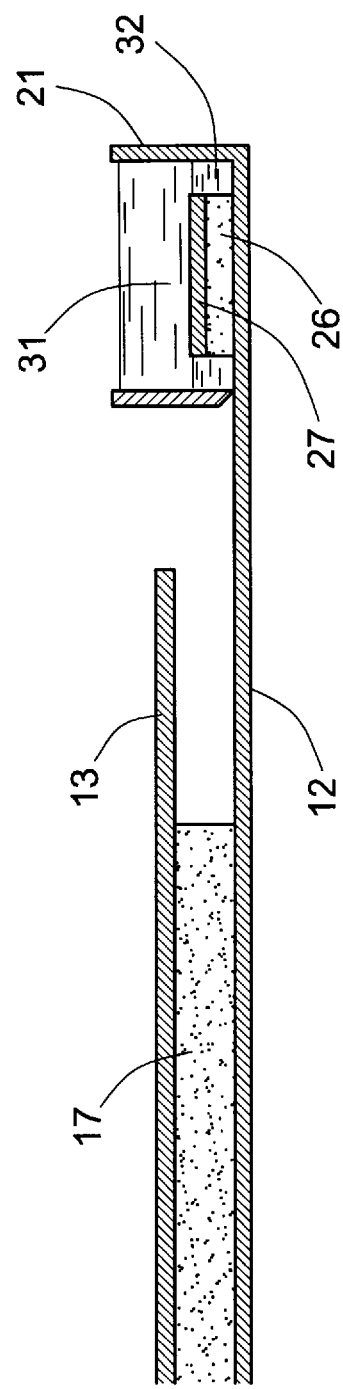
FIG. 3 is a longitudinal cross section similar to that of FIG. 2, showing the gel cassette being prepared for the first dimension separation.
Figure 4:
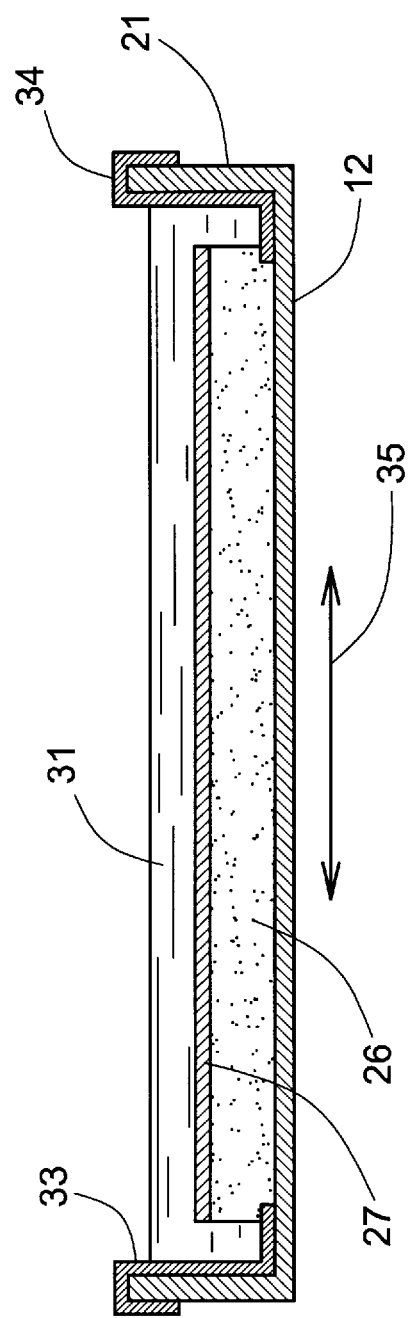
FIG. 4 is a transverse cross section of the gel cassette of FIG. 1, taken along the line 4—4 of FIG. 1, showing the gel during the first dimension separation.

FIGS. 3 and 4 show the cassette being prepared for use. The seal 25 is peeled away or otherwise removed, and oil 31 is added to the reservoir to cover the gel and its backing. A mixture of the sample and buffer 32 are then added. The oil 31 is selected as one that is immiscible with and of lower density than the sample and buffer mixture 32, and furthermore is not absorbed by the gel 26. The sample and buffer mixture 32 will then flow beneath the oil 31 to be absorbed by the gel, causing the gel to swell, while both the gel 26 and the sample and buffer mixture 32 are protected from the atmosphere by the oil 31. The amount of sample and buffer mixture placed in the reservoir in this manner will be selected such that the mixture is fully absorbed by the gel 26 and will cause substantially uniform swelling of the gel. It is not critical that the gel be uniformly swelled, and gels with less than uniform swelling can readily be used. A typical volume of sample and buffer mixture is 200 $\mu$L.

Once the gel is swelled with sample and buffer and allowed to equilibrate with the buffer for an appropriate period of time (generally an hour or two), electric current is passed through the swelled gel along its length to perform the first dimension separation. Electrical contacts between the power supply and the gel are supplied by conductive leads 33, 34 (FIG. 4) along the walls of the enclosure 21 and short distances along the contacting surface of the support plate 12. The direction of the electric field is indicated by the arrow 35. A typical voltage is 3,000 volts for 4 hours. Separation of the sample components occurs by isoelectric focusing, causing the components to group themselves into discrete zones whose locations along the length of the gel correspond to the charges (or isoelectric points) of the components. As alternatives to isoelectric focusing, electrophoretic migration of various kinds can be used, such as zone electrophoresis and other methods, with separation occurring on the basis of molecular size, charge, isoelectric points, or other distinguishing characteristics of the various species present in the sample. The procedure described up to this point is preferably conducted with the support plates 12, 13 in the horizontal position, although the procedure can also be conducted with the plates in the vertical position.

Once the first dimension separation has been completed, the oil 31 is removed from the reservoir, leaving the swelled gel containing the sample components located in zones spaced apart along the length of the gel. Buffer solution for the second dimension of the separation is then placed in the reservoir and the gel is permitted to equilibrate to this buffer for an appropriate period of time. Equilibration can for example consist of two fresh applications of the buffer for ten minutes each. The buffer may be a different buffer than that used for the first dimension separation.

Figure 5:
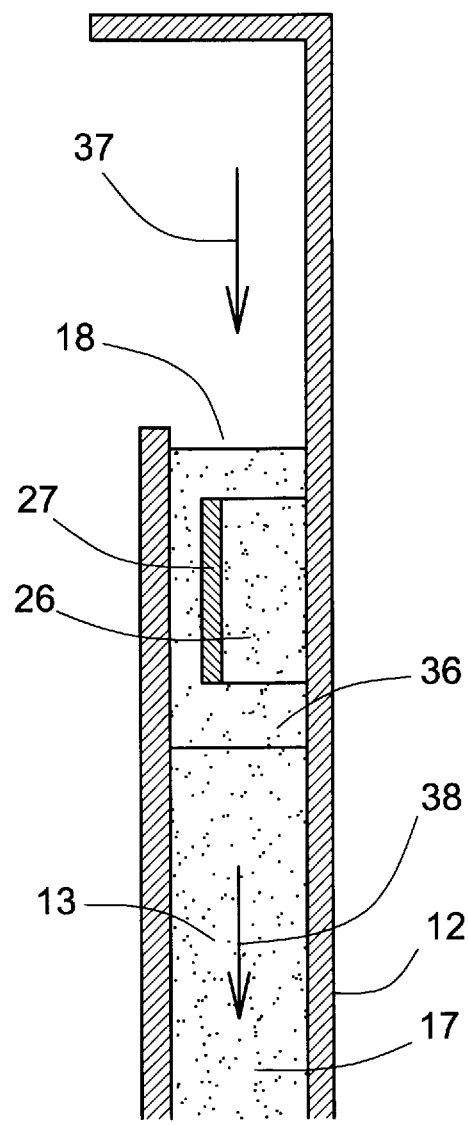
FIG. 5 is a longitudinal cross section similar to that of FIGS. 1 and 2, showing the gel cassette being prepared for the second dimension separation.

Once equilibration is completed, the equilibration buffer is removed, and the breakable wall 23 is removed. The cassette is then preferably rotated so that the support plates 12, 13 are vertical, as shown in FIG. 5, with the pH gradient gel positioned so that its longitudinal axis is horizontal. A gel-forming liquid material 36 such as hot agarose, mixed with the new buffer solution, is placed in the void space 18 between the support plates above the slab gel 17, and the strip gel 26 (which in some embodiments is a pH gradient gel), which contains the separated zones (as, for example in gradient gels, by isoelectric focusing), is then slid or otherwise urged down (as indicated by the arrow 37) into the liquid material 36, such that the two gels are in both fluid contact and electrical contact. Preferably, the strip gel 26 is fully immersed in the liquid. The liquid is then permitted to solidify, although the subsequent steps can also be performed while the material 36 remains in liquid form.

In either case, the cassette is then placed in a conventional electrophoresis cell designed for vertical slab gels. One example of a suitable electrophoresis cell is the Mini-PROTEAN® II Cell, a product of Bio-Rad Laboratories, Inc., Hercules, Calif., USA. Other electrophoresis cells that are likewise suitable are available from other commercial suppliers. Electrophoresis is then conducted by imposing an electric field in the direction shown by the arrow 38, causing the components within each first-dimension separated zone (i.e., each isoelectrically focused zone, in certain embodiments) to separate along vertical lanes within the gel.

The foregoing is offered primarily for purposes of illustration. It will be readily apparent to those skilled in the art that the physical configurations, materials, operating conditions, procedural steps and other parameters of the system and method described herein may be further modified or substituted in various ways without departing from the spirit and scope of the invention.

I claim:

1. A pre-cast two-dimensional electrophoresis gel system comprising a first electrophoretic separation medium in the form of an elongate strip and a second electrophoretic separation medium in the form of a slab, said elongate strip and said slab retained on a single support means and isolated from each other by a removable, fluid-impermeable, and electrically insulating barrier in which said elongate strip is encircled by walls forming a liquid-retaining receptacle, one of said walls being said removable, fluid-impermeable, and electrically insulating barrier.

2. A pre-cast two-dimensional electrophoresis gel system comprising a first electrophoretic separation medium in the form of an elongate strip and a second electrophoretic separation medium in the form of a slab, said elongate strip and said slab retained on a single support means and isolated from each other by a removable, fluid-impermeable, and electrically insulating barrier in which said elongate strip is encased in an enclosure completely isolating said first electrophoretic separation medium from access to environmental air, one wall of said enclosure being said removable fluid-impermeable, and electrically insulating barrier, and another wall of said enclosure being a removable, moisture-impermeable seal.

3. A pre-cast two-dimensional electrophoresis gel system comprising a first electrophoretic separation medium in the form of an elongate strip and a second electrophoretic separation medium in the form of a slab, said elongate strip and said slab retained on a single support means and isolated from each other by a removable, fluid-impermeable, and electrically insulating barrier in which said elongate strip is a dry gel that is swellable upon imbibition of an aqueous liquid.

4. A pre-cast two-dimensional electrophoresis gel system in accordance with claims 1, 2 or 3 in which said single support means is a pair of substantially parallel support plates.

5. A pre-cast two-dimensional electrophoresis gel system in accordance with claims 1, 2 or 3 in which said elongate strip and said slab are polyacrylamide gels.

6. A pre-cast two-dimensional electrophoresis gel system in accordance with claims 1, 2 or 3 in which said elongate strip contains charged groups immobilized thereon in a selected distribution to form a fixed pH gradient extending lengthwise thereon.

7. A method for separating a sample into components by two-dimensional electrophoresis, said method comprising:
(a) loading said sample onto a first electrophoretic separation medium of a two-dimensional electrophoresis arrangement comprising first and second electrophoretic separation media, said first electrophoretic separation medium being in the form of an elongate strip and said second electrophoretic separation medium in the form of a slab, said elongate strip and said slab retained on a single support means and isolated from each other by a removable, fluid-impermeable, and electrically insulated barrier;

(b) imposing an electric field across said elongate strip to divide said sample components into zones spaced alone said elongate strip;

(c) removing said barrier and placing all zones in said elongate strip in electrical and fluid contact with said slab; and (d) imposing an electric field across both said elongate strip and said slab in a direction perpendicular to said elongate strip, to effect electrophoretic separation of said zones in said slab in which said elongate strip is encircles by walls forming a liquid-retaining receptacle, one of said walls being said removable, fluid-impermeable, and electrically insulating barrier, and (a) comprises placing said sample inside said liquid-retaining receptacle in fluid contact with said elongate strip.

8. A method in accordance with claim 7 in which (a) further comprises diluting said sample in an aqueous buffer solution, covering said elongate strip with a water-immiscible liquid of a density lower than that of said buffer solution, and placing said buffer solution containing said sample inside said liquid-retaining receptacle such that said buffer solution, sample and elongate strip are covered by said water-immiscible liquid.

9. A method in accordance with claim 7 in which said single support means is comprised of first and second substantially parallel support plates with a gap therebetween and said slab in said gap, said first support plate having an exposed strip extending beyond one edge of said second support plate, with said elongate strip adhered to said exposed strip, and (c) comprises moving said elongate strip into said gap to contact said slab.

10. A method in accordance with claim 7 in which said elongate strip contains charged groups immobilized thereon in a selected distribution to form a fixed pH gradient extending lengthwise thereon, and (b) comprises dividing said sample components into zones by isoelectric focusing.

* * * * *